(12) United States Patent
Li et al.

(10) Patent No.: US 11,688,494 B2
(45) Date of Patent: Jun. 27, 2023

(54) CROSS-ORGANIZATION DATA INSTANCE MATCHING

(71) Applicant: INTERNATIONAL BUSINESS MACHINES CORPORATION, Armonk, NY (US)

(72) Inventors: Ying Xue Li, Beijing (CN); Wen Sun, Beijing (CN); Jing Mei, Beijing (CN); Yi Qin Yu, Beijing (CN); Bibo Hao, Beijing (CN); Jian Min Jiang, Beijing (CN); Guo Tong Xie, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1016 days.

(21) Appl. No.: 16/139,678

(22) Filed: Sep. 24, 2018

(65) Prior Publication Data

US 2020/0098453 A1   Mar. 26, 2020

(51) Int. Cl.
*G16H 10/60* (2018.01)
*G06F 16/28* (2019.01)
*G16H 15/00* (2018.01)

(52) U.S. Cl.
CPC .......... *G16H 10/60* (2018.01); *G06F 16/285* (2019.01); *G16H 15/00* (2018.01)

(58) Field of Classification Search
CPC ....... G16H 10/60; G16H 15/00; G06F 16/285
See application file for complete search history.

(56) References Cited

U.S. PATENT DOCUMENTS

| | | | |
|---|---|---|---|
| 2005/0049497 A1* | 3/2005 | Krishnan | G16H 50/20 600/437 |
| 2013/0080192 A1 | 3/2013 | Bucur et al. | |
| 2015/0025908 A1* | 1/2015 | Lakshminarayan | G16H 10/60 705/3 |
| 2016/0210427 A1 | 7/2016 | Mynhier et al. | |
| 2017/0192967 A1 | 7/2017 | Gilder et al. | |

FOREIGN PATENT DOCUMENTS

WO    2014182725 A1    11/2014

\* cited by examiner

*Primary Examiner* — Michael Tomaszewski
*Assistant Examiner* — Mohmad Muqueeth
(74) *Attorney, Agent, or Firm* — Tutunjian & Bitetto, P.C.; Peter Edwards

(57) ABSTRACT

The disclosure provides a method for data instance processing. The method includes obtaining a set of data instances collected from a plurality of organizations. Each of the data instances includes at least one record formed in an organization that stores values of a plurality of attributes of the data instance. The method also includes dividing the set of data instances into groups, wherein data instances with conflicting values for the same attribute are divided into different groups. The method further includes subdividing data instances in each of the groups into clusters.

20 Claims, 6 Drawing Sheets

| Instance 1 | Name | Gender | Insurance Type | Diagnosis | Weight Index | Systolic Pressure |
|---|---|---|---|---|---|---|
| 20160101 | Jack | 0 | Commercial | N/A | 20.1 | 116 |
| 20170101 | Jack | 0 | Commercial | Gigantism | 20.1 | 116 |
| 20180101 | Jack | N/A | Commercial | CHD | 20.1 | 116 |

| Instance 2 | Name | Gender | Insurance Type | Diagnosis | Weight Index | Systolic Pressure |
|---|---|---|---|---|---|---|
| 20160201 | Jack | 0 | Commercial | Gigantism | 20.2 | 118 |
| 20180101 | Jack | N/A | Commercial | Hyperlipidemia | 20.2 | 118 |

| Instance 3 | Name | Gender | Insurance Type | Diagnosis | Weight Index | Systolic Pressure |
|---|---|---|---|---|---|---|
| 20160301 | Jack | 0 | Commercial | Gigantism | 20.3 | 180 |
| 20170301 | Jack | 0 | Commercial | N/A | 20.3 | 168 |
| 20180301 | Jack | N/A | Commercial | Hyperlipidemia | 20.3 | 192 |

| Instance 4 | Name | Gender | Insurance Type | Diagnosis | Weight Index | Systolic Pressure |
|---|---|---|---|---|---|---|
| 20160401 | Jack | 0 | Commercial | N/A | 20.4 | 190 |
| 20170401 | Jack | 0 | Commercial | Hyperlipidemia | 20.4 | 189 |
| 20180401 | Jack | N/A | Commercial | N/A | 20.4 | 188 |

| Instance 5 | Name | Gender | Insurance Type | Diagnosis | Weight Index | Systolic Pressure |
|---|---|---|---|---|---|---|
| 20160501 | Jack | 0 | Medicare | N/A | 27.8 | 118 |
| 20170501 | Jack | 0 | N/A | Hyperlipidemia | 27.8 | 118 |
| 20180501 | Jack | N/A | Medicare | CHD | 27.8 | 118 |

| Instance 6 | Name | Gender | Insurance Type | Diagnosis | Weight Index | Systolic Pressure |
|---|---|---|---|---|---|---|
| 20160601 | Jack | 0 | Medicare | N/A | 27.9 | 120 |
| 20170601 | Jack | 0 | N/A | Dwarfism | 27.9 | 117 |
| 20180601 | Jack | N/A | N/A | Diabetes | 27.9 | 120 |

| Instance 7 | Name | Gender | Insurance Type | Diagnosis | Weight Index | Systolic Pressure |
|---|---|---|---|---|---|---|
| 20160701 | Jack | 0 | Commercial | Dwarfism | 28.1 | 120 |
| 20170701 | Jack | 0 | Commercial | N/A | 28.1 | 117 |
| 20180701 | Jack | N/A | Commercial | Diabetes | 28.1 | 117 |

| Instance 8 | Name | Gender | Insurance Type | Diagnosis | Weight Index | Systolic Pressure |
|---|---|---|---|---|---|---|
| 20160801 | Jack | 0 | Commercial | N/A | 28.1 | 118 |
| 20170801 | Jack | 0 | Commercial | N/A | 28 | 116 |
| 20180801 | Jack | N/A | Commercial | Dwarfism | 28.2 | 117 |

CROSS-ORGANIZATION DATA INSTANCE MATCHING

BACKGROUND

Technical Field

The present invention generally relates to data integration, and more specifically, to a method, a system and a computer program product for cross-organization data instance matching.

Description of the Related Art

In the big data era, there is a need for matching data instances across multiple organizations. For example, for a big data analysis, patient information can be collected from multiple hospitals, purchasing information can be collected from multiple on-line shops, or player information can be collected from multiple game sites. Taking the patient information as an example, matching patients accurately across multiple organizations is one of the crucial prerequisites for healthcare data integration. That is, healthcare data integration systems need to determine which pieces of patient information from different hospitals belong to the same person. However, some important but sensitive information such as IDs or Social Security Numbers (SSNs), or birth dates of patients cannot be shared between organizations

SUMMARY

In this disclosure, a method, a system and a computer program product are provided for cross-organization data instance matching.

According to one embodiment of the present invention, a method is provided for data instance processing. The method includes obtaining a set of data instances collected from a plurality of organizations. Each of the data instances includes at least one record formed in an organization that stores values of a plurality of attributes of the data instance. The method also includes dividing the set of data instances into groups. Data instances with conflicting values for the same attribute are divided into different groups. The method further includes subdividing data instances in each of the groups into clusters.

According to another embodiment of the present invention, a system is provided for data instance processing. The system includes one or more processors and a memory coupled to at least one of the one or more processors. The system has a set of computer program instructions stored in the memory and executed by at least one of the one or more processors in order to perform action of obtaining a set of data instances collected from a plurality of organizations. Each of the data instances includes at least one record formed in an organization that stores values of a plurality of attributes of the data instance. The system also includes a set of computer program instructions stored in the memory and executed by at least one of the one or more processors in order to perform action of dividing the set of data instances into groups. Data instances with conflicting values for the same attribute are divided into different groups. The system further includes a set of computer program instructions stored in the memory and executed by at least one of the one or more processors in order to perform action of subdividing data instances in each of the groups into clusters.

According to a further embodiment of the present invention, a computer program product is provided for data instance processing. The computer program product includes a computer readable storage medium having program instructions embodied therewith. The program instructions are executable by a device to cause the device to perform a method. The method includes obtaining a set of data instances collected from a plurality of organizations. Each of the data instances includes at least one record formed in an organization that stores values of a plurality of attributes of the data instance. The method also includes dividing the set of data instances into groups. Data instances with conflicting values for the same attribute are divided into different groups. The method further includes subdividing data instances in each of the groups into clusters.

BRIEF DESCRIPTION OF THE DRAWINGS

The following description will provide details of preferred embodiments with reference to the following figures wherein:

FIG. 4 is a flowchart illustrating a method for data instance processing according to an embodiment of the present invention.

FIGS. 5A and 5B illustrate an example set of patient instances that are collected from a plurality of medical organizations and might describe the same patient.

DETAILED DESCRIPTION

Figure 1:
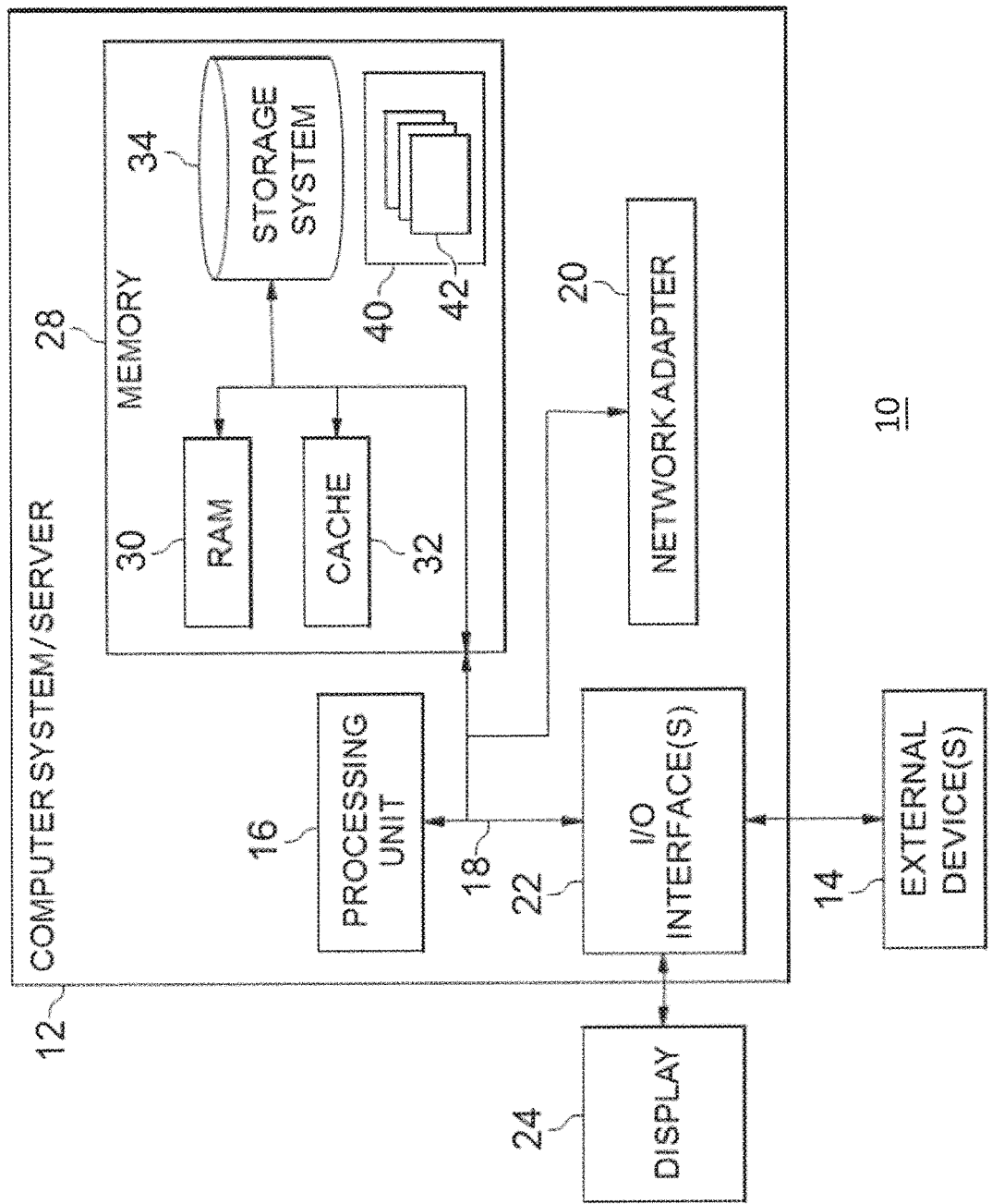
FIG. 1 depicts a cloud computing node according to an embodiment of the present invention.

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Additionally, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
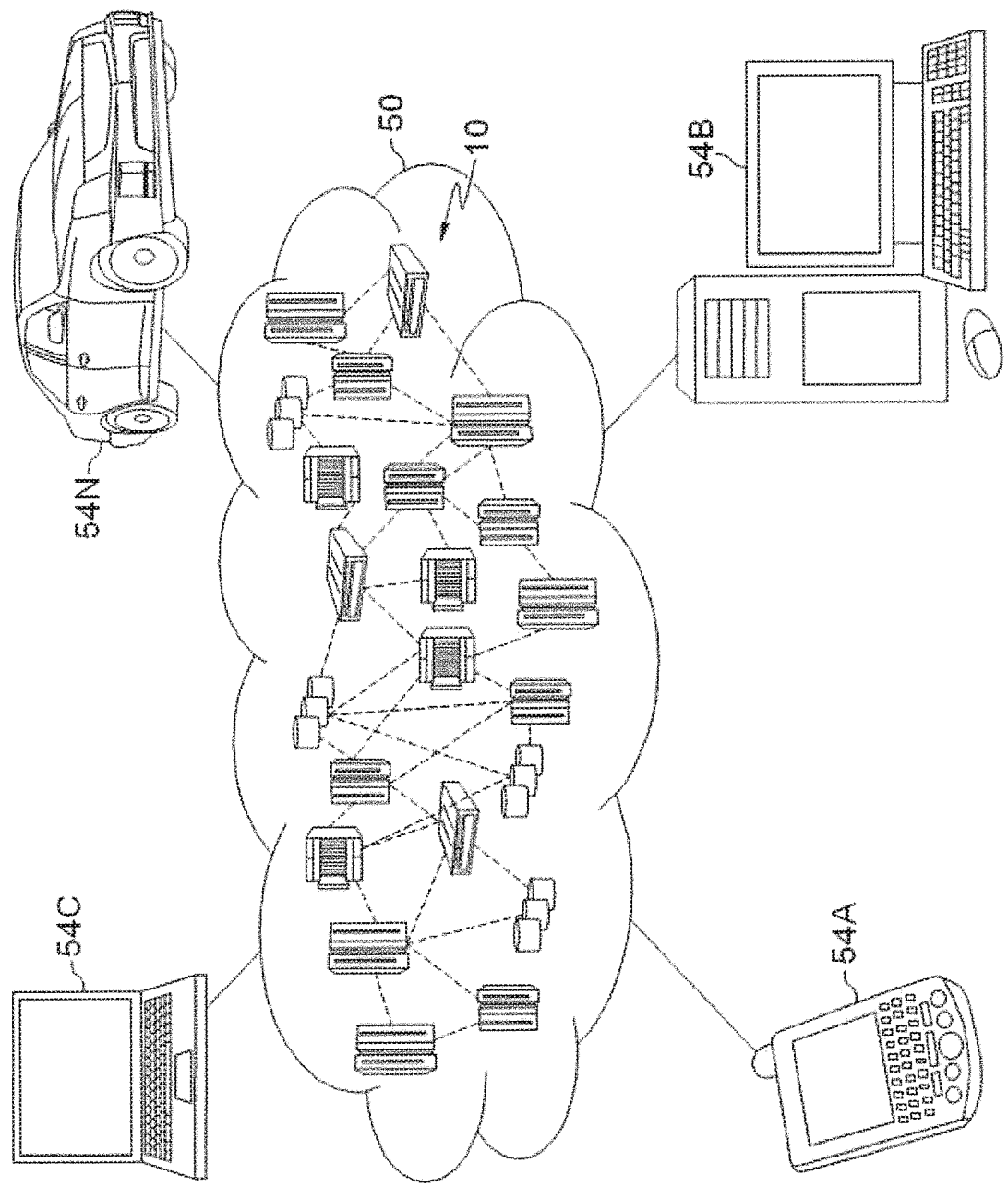
FIG. 2 depicts a cloud computing environment according to an embodiment of the present invention.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
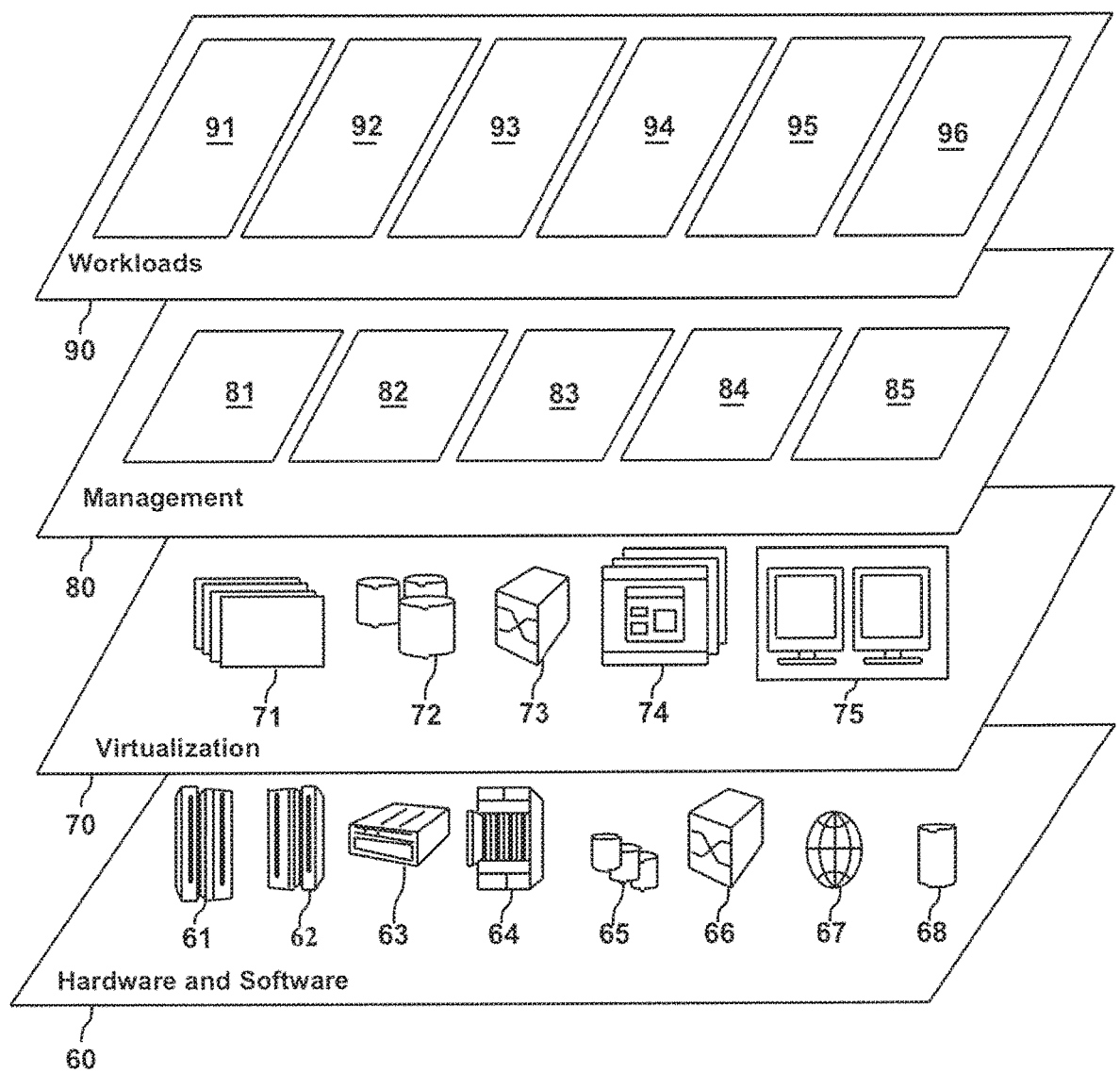
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and cross-organization data instance matching 96.

Currently, taking the patient instances as an example, two kinds of algorithms have been used to perform cross-organization patient matching. One kind of algorithms are deterministic matching algorithms that perform a character-by-character comparison on one or more demographic attributes of patient instances. The other kind of algorithms are probabilistic matching algorithms that calculate a probability for each patient pair with some statistical approaches on some demographic attributes. The two kinds of algorithms only utilize demographic information of patients to perform cross-organization patient matching.

It is noted that, both of the two kinds of current matching algorithms only utilize demographic information. However, for the sake of privacy protection, demographic information is usually limited, which sometimes hinder the cross-organization data instance matching. Additionally, when the number of data instances (for example, patient instances, player instances, purchaser instances, passenger instances, and student instances, etc.) becomes larger, because probability of coincidence increases, matching accuracy degrades. In this case, to meet a requisite accuracy, large amount of labor work is needed to cure the matching result, which is quite troublesome and time-consuming.

The present invention discloses a new method to perform the cross-organization data instance matching. A two-stage method is disclosed in which a preliminary division is performed by conflict detection and then a precise division is performed based on clustering.

Figures 4, 5A:
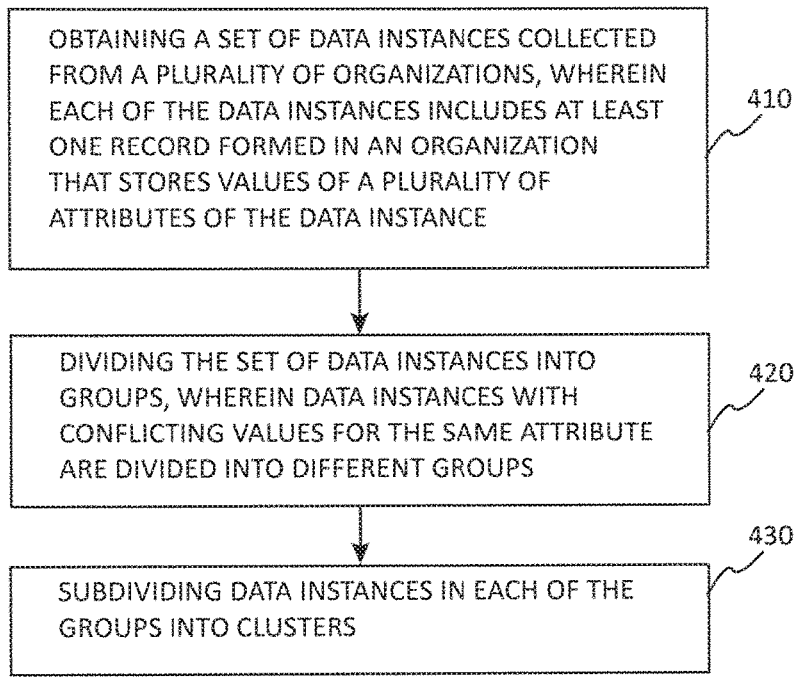

With reference now to FIG. 4, a flowchart illustrates a method for data instance processing according to an embodiment of the present invention. As shown in FIG. 4, the method for data instance matching includes a data instance receiving step 410, a preliminary division step 420, and a precise division step 430. In one embodiment of the invention, the method in FIG. 4 can be performed in the cloud computing node as shown in FIG. 1.

To better describe the present invention, patient instances are used as examples to explain the method in FIG. 4. However, the method is not limited to matching of patient instances, and can be applied to matching of other data instances such as player instances, purchaser instances, or passenger instances, for the purpose of big data analysis.

When the method in FIG. 4 begins, in the data instance receiving step 410, a set of data instances collected from a plurality of organizations is obtained. Each of the data instances may include at least one record formed in an organization that stores values of a plurality of attributes of the data instance. For example, a data instance such as a patient instance is shown below.

TABLE 1

| | Name | Gender | Insurance Type | Diagnosis | Weight Index | Systolic Pressure |
|---|---|---|---|---|---|---|
| 20160101 | Jack | 0 | Commercial | N/A | 20.1 | 116 |
| 20170101 | Jack | 0 | Commercial | Gigantism | 20.1 | 116 |
| 20180101 | Jack | N/A | Commercial | CHD | 20.1 | 116 |

As shown in Table 1, a patient instance includes patient records of an individual (herein Jack) from one medical organization. In table 1, the patient instance of Jack has three medical records formed in the same medical organization. The three medical records were generated due to Jack's visits to this medical organization on three different dates. In other words, the patient instance in Table 1 reflects a medical history of Jack at this specific medical organization.

It can be seen from Table 1 that, a patient instance includes a plurality of attributes such as "Name", "Gender", "Insurance Type", "Diagnosis", "Weight Index" and "Systolic Pressure". The plurality of attributes may include at least one demographic attribute and at least one clinical attribute. For example, in Table 1, "Name", "Gender" and "Insurance Type" belong to demographic attributes; and "Diagnosis", "Weight Index" and "Systolic Pressure" belong to clinical attributes. In the records, not every attribute has a value. For example, in Table 1, the attribute "Gender" in the record dated "20180101" and the attribute "Diagnosis" in the record dated "20160101" is not available and labeled as "N/A". Additionally, "CHD" in Table 1 is acronym of coronary heart disease. Table 1 is only an example of patient instance, those skilled in the art know that other attributes can be included in a patient instance.

According to one embodiment of the invention, the set of data instances may be patient instances that are collected because they might describe the same patient. FIGS. 5A and 5B illustrate an example set of patient instances that are collected from a plurality of medical organizations and might describe the same patient, e.g., Jack. FIGS. 5A and 5B show eight patient instances from eight medical organization. The eight patient instances are collected as a set because they share the same patient's name "Jack", which means these patient instances might come from the same patient. And the task here is to divide the set of data instances into groups if "Jack" is a name of actual different patients so that each group only includes patient instances from an actual individual patient. The set of patient instances in FIGS. 5A and 5B will be used to explain the method in FIG. 4. It is noted that, since patient instances are collected from different medical organizations, they may have different attributes. For example, some patient instances may have an attribute of "birth date" or "blood type", but other patient instances might not have these attributes. The patient instances in FIGS. 5A and 5B having the same attributes are only used as examples to simplify the description.

In the preliminary division step 420, the set of data instances are divided into groups, wherein data instances with conflicting values for the same attribute are divided into different groups. Dividing the set of data instances into groups further includes for each data instance in the set of data instances, forming a value sequence based on the at least one record of the data instance. In one embodiment of the invention, the value sequence may include selected attributes as its elements, that is, not all the attributes of the patient instance are used to form this value sequence. For example, a value sequence of a data instance may have the form of [select_attr0, select_attr1, . . . , select_attrN].

Taking the set of patient instances 500 and 501 in FIGS. 5A and 5B, respectively, as examples to explain how to form the value sequence. For patient instances from different medical organizations, relevant and common demographic and clinic attributes are extracted to form elements of value sequences. In one example, attributes "Insurance Type", "Diagnosis", "Weight Index" and "Systolic Pressure" can be selected to form the value sequence. For the two patient instances represented in the set of patent instances 500 in FIG. 5A and the six patient instances represented in the set of patent instances 501 in FIG. 5B, the following value sequences can be formed.

TABLE 2

| Instance | Insurance Type | Diagnosis_Gigantism | Diagnosis_Dwarfism | Diagnosis_CHD | Weight Index | Systolic Pressure |
|---|---|---|---|---|---|---|
| 1 | Commercial | 1 | 0 | 1 | 20.1 | 116 |
| 2 | Commercial | 1 | 0 | 0 | 20.2 | 118 |
| 3 | Commercial | 1 | 0 | 0 | 20.3 | 180 |
| 4 | Commercial | 0 | 0 | 0 | 20.4 | 189 |

TABLE 2-continued

| Instance | Insurance Type | Diagnosis_Gigantism | Diagnosis_Dwarfism | Diagnosis_CHD | Weight Index | Systolic Pressure |
|---|---|---|---|---|---|---|
| 5 | Medicare | 0 | 0 | 1 | 27.8 | 118 |
| 6 | Medicare | 0 | 1 | 0 | 27.9 | 119 |
| 7 | Commercial | 0 | 1 | 0 | 28.1 | 118 |
| 8 | Commercial | 0 | 1 | 0 | 28.1 | 117 |

In the above Table 2, each row represents a value sequence for a patient instance. Eight value sequences in Table 2 are formed for the eight patient instances in FIGS. 5A and 5B. Here, the attribute "Diagnosis" is expanded to three elements "Diagnosis_Gigantism", "Diagnosis_Dwarfism", and "Diagnosis_CHD" in a value sequence. The objective of forming the value sequence is to obtain a single value for each attribute (or sub-attribute) of a patient instance. In one embodiment of the invention, if a patient has ever been diagnosed as having a disease in his/her medical records in a patient instance, the element corresponding to this disease in the value sequence of the patient instance will be set to 1; and if a patient has never been diagnosed as having a disease in his/her medical records in a patient instance, the element corresponding to this disease in the value sequence of the patient instance will be set to 0. Other binary values can also be used to indicate whether a disease exists, such as "Yes" or "No". In this example, some diagnoses are not used to form the values sequences, such as hyperlipidemia and diabetes, which depends on selection of users.

In one embodiment of the invention, if an attribute has a value of enumeration type, value of the attribute in the value sequence can be determined based on the value of the attribute that dominates in medical records of the patient instance. That is, the value of the attribute with the highest frequency will be determined as value of the attribute in the value sequence. For example, values of "Insurance Type" in value sequences in Table 2 are of enumeration type, and are determined based on frequency of various values existing in the records of respective patient instances. Here, "N/A" is excluded from computation of frequency since it is an invalid value. For example, for instance 6, only "Medicare" appears once in its three records, so the attribute "Insurance Type" of this instance in its value sequence in Table 2 is determined as "Medicare".

In one embodiment of the invention, if an attribute has a value of numeral type, an average or variance of all values of an attribute in in medical records of a patient instance can be determined as value of the attribute in the value sequence. For example, values of "Weight Index" and "Systolic Pressure" in value sequences in Table 2 are of numeral type, and are determined as an average of corresponding values in medical records. For example, for instance 3, the attribute "Systolic Pressure" of this instance in its value sequence in Table 2 is determined as an average of 180, 168 and 192, that is, 180; and for instance 8, the attribute "Weight Index" of this instance in its value sequence in Table 2 is determined as an average of 28.1, 28 and 28.2, that is, 28.1.

Figure 6:
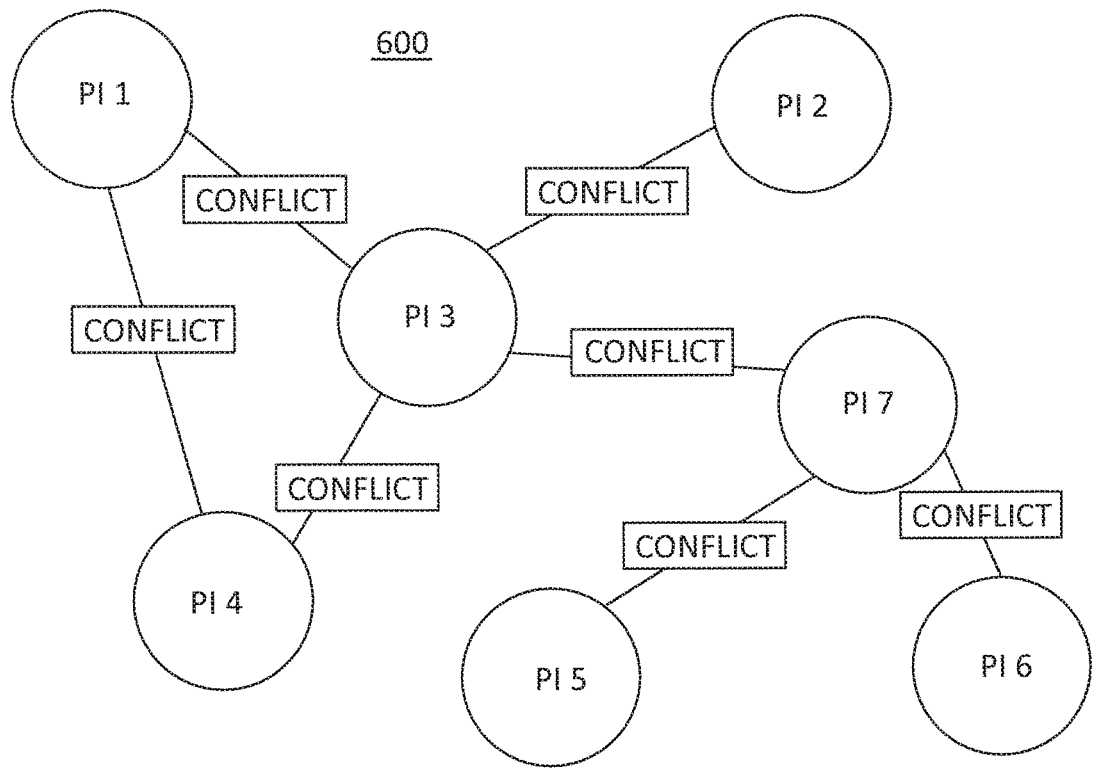
FIG. 6 shows an example of a conflict network according to an embodiment of the present invention.

Next, the formed values sequences may be compared with each other based on some predetermined rules to perform conflict detection. In one embodiment of the invention, a conflict network may be constructed in which a data instance is represented by a node and there is an edge between two nodes if two data instances represented by the two nodes have at least one conflicting element in their value sequences. Conflict happens between two patient instances if any of attributes in their value sequences has a conflict. For different types of attributes, conflict rules are different. In one embodiment of the invention, for an attribute of character type such as name or of date type such as birth date, the rule may be that, if the values of the attribute from two value sequences are not equal, a conflict exists; for an attribute of numeral type, the rule may be that, if the difference between values of the attribute from two value sequences is greater than a threshold, a conflict exists. These are only two examples for rules, and other rules can also be applied. FIG. 6 shows an example of a conflict network 600 in which seven patient instances (PI1, PI2, PI3, PI4, PI5, PI6, PI7) are shown as nodes and there is an edge between two nodes if patient instances represented by them have a conflict. For example, in FIG. 6, node PI3 has edges with nodes PI1, PI2, PI4 and PI7, which means patient instance 3 has conflicts with patient instances 1, 2, 4 and 7.

Taking the patient instances in FIGS. 5A and 5B and the value sequences in Table 2 as examples, the following rules may be applied, for example.

Rule 1: A patient cannot have both gigantism and dwarfism.

Rule 2: A patient's insurance type should be consistent.

Rule 1 means a patient instance with a gigantism diagnosis has a conflict with a patient instance with a dwarfism diagnosis. That is, they do not belong to a single patient. Rule 2 means a patient instance with a commercial insurance has a conflict with a patient instance with a Medicare. That is, they do not belong to a single patient. Using these rules, a conflict network can be constructed in which there are eight nodes 1-8 representing patient instances 1-8 and an edge exists between two nodes if two patient instances represented by the two nodes have a conflict. In one embodiment of the invention, for the example in Table 2 and Rules 1 and 2, we can obtain the following bitmap:

TABLE 3

| Instance (Node) | 1 | 2 | 3 | 4 | 5 | 6 | 7 | 8 |
|---|---|---|---|---|---|---|---|---|
| 1 | N/A | 0 | 0 | 0 | 1 | 1 | 1 | 1 |
| 2 | 0 | N/A | 0 | 0 | 1 | 1 | 1 | 1 |
| 3 | 0 | 0 | N/A | 0 | 1 | 1 | 1 | 1 |
| 4 | 0 | 0 | 0 | N/A | 1 | 1 | 0 | 0 |
| 5 | 1 | 1 | 1 | 1 | N/A | 0 | 1 | 1 |
| 6 | 1 | 1 | 1 | 1 | 0 | N/A | 1 | 1 |
| 7 | 1 | 1 | 1 | 0 | 1 | 1 | N/A | 0 |
| 8 | 1 | 1 | 1 | 0 | 1 | 1 | 0 | N/A |

In Table 3, a cell with a coordinate (x, y) is set to 1 if the instance (or node) labeled by row number x and the instance (or node) labeled by column number y have a conflict; and a cell with a coordinate (x, y) is set to 0 if the instance (or node) labeled by row number x and the instance (or node) labeled by column number y do not have a conflict. The bitmap in Table 3 may be a form of data structure to represent a conflict network.

With a conflict network, then, nodes of the conflict network may be assigned with minimum labels, wherein nodes directly connected by an edge in the conflict network have different labels. Through the label assigning, data instances represented by nodes with a same label are divided into a same group. In one embodiment of the invention, coloring algorithm may be used to perform the label assigning. The coloring algorithm is a known algorithm in graph theory. For example, through the coloring, the example in FIG. 6 will be colored with three different colors, and nodes with the same color will form a group. That is, the following three groups are formed: (PI1, PI2, PI7), (PI3, PI5), (PI4, PI6). For the example in FIGS. 5A and 5B, the performance of the coloring algorithm might result in three groups: Group 1: Patient Instances 1, 2, 3, 4; Group 2: Patient Instances 5, 6; and Group 3: Patient Instances 7, 8.

Though in the above examples the coloring algorithm is used to perform the preliminary division. However, other algorithms can be also applied as long as instances with conflicting attribute value(s) can be divided into separate groups.

Now referring back to FIG. 4, in the precise division step 430, data instances in each of the groups are subdivided into clusters. Data instances in each cluster are deemed as from the same single entity. In one embodiment of the invention, subdividing data instances in each of the groups into clusters further includes: constructing, for each of the data instances in the group, a feature vector based on the at least one record of the data instance. In one embodiment of the invention, the feature vector is a vector with all its elements transformed into binary values. That is, in one embodiment of the invention, values of attributes stored in the at least one record of the data instance may be transformed into binary values if they are not. For example, for a continuous value, it can be generalized as a binary value or be divided into several intervals. Taking systolic pressure as an example, it is a continuous value. In one example, it can be generalized as normal (1) or abnormal (0); and in another example, it can be discretized as high pressure (11), middle pressure (10) and low pressure (01).

Figure 7:
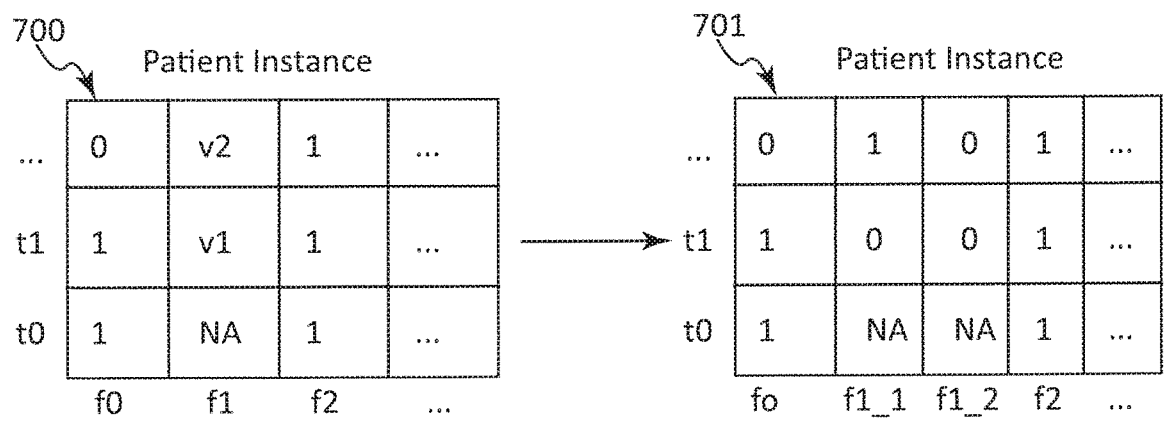
FIG. 7 shows an example of splitting an attribute into two during construction of a feature vector according to one embodiment of the present invention.

In one embodiment of the invention, a first attribute of the plurality of attributes may be split into a plurality of second attributes so that each of the plurality of second attributes may be used to construct an element of the feature vector. For the above example in which systolic pressure is discretized as three binary values, the binary representation of systolic pressure occupies two bits and each bit constructs an element of the feature vector. FIG. 7 shows an example of splitting an attribute into two during construction of a feature vector according to one embodiment of the invention. In FIG. 7, the patient instance 700 has at least three records, each row represents a record, and attribute f1 has a continuous value (v1, v2). To construct the feature vector, attribute f is split into two attributes f1_1 and f1_2, as shown in patient instance 701. Each of the two attributes f1_1 and f1_2 is a bit and the combination of f1_1 and f1_2 represents a discretization of continuous value. For example, in patient instance 700, v2 is discretized as 10 and v1 is discretized as 00 as shown in patient instance 701. Normally, the attribute being split is a clinical attribute.

In another embodiment, elements of the feature vector of a patient instance can be calculated from records of the patient instance. For example, the following equation can be used to calculate an element of the feature vector:

$$fvalue(p) = Freq(f, instance) * Freq(f, group)$$

Herein, fvalue(p) indicates the feature vector of patient instance p, Freq(f, instance) indicates ratio of valid values (e.g., non-NA values) of attribute f in records of the patient instance, and $$Freq(f, group) = \log\frac{N}{M},$$

wherein N is number of patient instances with values on f in the group and M is number of patient instances with values "1s" on f in the group. By constructing a feature vector in this way, a clinical pattern may be introduced into the feature vector, which is useful for applying unsupervised learning algorithm.

Though in the above embodiment the clinical pattern is introduced, a simple discretization, as described above, can be used to construct a feature vector. For example, for the example in FIGS. 5A and 5B, the following feature vectors can be constructed.

TABLE 4

| Vector of Instance | Insurance Type | Diag_1 | Diag_2 | Diag_3 | Diag_4 | Diag_5 | WI_overweight | SP_abnormal |
|---|---|---|---|---|---|---|---|---|
| 1 | 0 | 1 | 0 | 0 | 1 | 0 | 0 | 0 |
| 2 | 0 | 1 | 0 | 1 | 0 | 0 | 0 | 0 |
| 3 | 0 | 0 | 0 | 1 | 0 | 0 | 0 | 1 |
| 4 | 0 | 0 | 0 | 1 | 0 | 0 | 0 | 1 |
| 5 | 1 | 0 | 0 | 1 | 1 | 0 | 1 | 0 |
| 6 | 1 | 0 | 1 | 0 | 0 | 1 | 1 | 0 |
| 7 | 0 | 0 | 1 | 0 | 0 | 1 | 1 | 0 |
| 8 | 0 | 0 | 1 | 0 | 0 | 0 | 1 | 0 |

In Table 4, each row represents a feature vector of a patient instance in FIGS. 5A and 5B. For example, the feature vector {0, 1, 0, 0, 1, 0, 0, 0} in the first row corresponds to patient instance 1 in FIG. 5A. In Table 4, attribute "Insurance Type" is binarized so that "1" represents Medicare and "0" represents commercial insurance. "Diag_1" to "Diag_5" represents diagnosis on gigantism, diagnosis on dwarfism, diagnosis on hyperlipidemia, diagnosis on CHD and diagnosis on diabetes, respectively. "WI_overweight" indicates if the patient is overweight, which is based on a comparison between his/her weight index and a threshold. "SP_abnormal" indicates if the patient's systolic pressure is abnormal, which is based on a comparison between his/her systolic pressure and a threshold.

With the constructed feature vector that characterizes a patient instance, distances between every two feature vectors can be calculated. Here, an Euclidean distance, a Mahalanobis distance or other distance can be calculated. At last, the data instances in the group are clustered into clusters based on the calculated distances. The clustering algorithm can be one of K-Means, K-Medoids, Gaussian Mixture Model (GMM), Spectral clustering, Ncut, and etc. Patient instances in the same cluster refer to one identical person. Thus the patient instances in the same cluster may be combined into a new patient record, for example, reflecting the data represented in the patient instances collected in to the cluster.

Taking patient instances in FIGS. 5A and 5B as an example, after the precise division, that is, after the clustering, Groups 2 and 3 are not further divided, and patient instances in Group 1 are subdivided into two clusters: (patient instance 1, patient instance 2), (patient instance 3, patient instance 4).

The application of the invention can increase accuracy of matching and reduce labor work needed to cure the matching result.

The present invention, when applied to patient health records, for example, may improve healthcare outcomes for patients by collecting health records for an individual from the various healthcare providers to which the individual has visited. Having all the health records for an individual combined may further increase the likelihood that medical conditions are not overlooked and/or are properly diagnosed. Accordingly, medical professionals are required to devote less time to either retrieving health records or re-evaluating the patient for previously diagnosed condition. As a result, medical costs, both to the healthcare provider and the patient may be reduced.

Moreover, implementation of the present invention reduces workload and increases efficiency of the computer systems and networks related to the healthcare providers and organizations, since maintaining complete and up-to-date records may relieve the computer systems and networks of the need to request and process data from external sources during patient visits. Further, multiple records for the same individual may be combined, which reduces the number of records needing to be stored in a database, and thus may reduce the memory requirements for the database.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may have copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for two-stage data instance processing, the method comprising:
    obtaining, by one or more processors, a set of data instances collected from a plurality of organizations over a network, wherein each of the data instances includes at least one record formed in an organization that stores values of a plurality of attributes of the data instance;
    preliminarily dividing, in stage one, by conflict detection using one or more processors, the set of data instances into groups, wherein data instances with conflicting values for the same attribute are divided into different groups and stored on a remote server in a distributed cloud computing environment;
    subdividing, in stage two, by one or more processors, data instances in each of the groups into clusters to increase precision of the dividing, the subdividing comprising constructing, by one or more processors, for each of the data instances in the groups, a feature vector based on the at least one record of the data instance for further processing, with the values of the plurality of attributes being transformed into binary values for increased efficiency of the processing and minimization of bandwidth and memory requirements; and
    creating a new electronic record comprising the transformed binary values of the plurality of attributes of the data instances in the cluster by combining the data instances in each cluster, the electronic record being updated on a local machine and stored on the remote server in the distributed cloud computing environment to minimize network bandwidth and memory requirements for efficient iterative accessing and maintaining of the record.

2. The method according to claim 1, wherein dividing the set of data instances into groups further includes:
    for each data instance in the set of data instances, forming, by one or more processors, a value sequence based on the at least one record of the data instance, wherein the value sequence includes selected attributes as its elements;
    constructing, by one or more processors, a conflict network in which a data instance is represented by a node and there is an edge between two nodes if two data instances represented by the two nodes have at least one conflicting element in their value sequences; and
    assigning, by one or more processors, labels to nodes of the conflict network with minimum labels, wherein nodes directly connected by an edge in the conflict network have different labels, and data instances represented by nodes with a same label are divided into a same group.

3. The method according to claim 1, wherein subdividing data instances in each of the groups into clusters further includes:
    calculating, by one or more processors, distances between every two feature vectors; and
    clustering, by one or more processors, the data instances in each of the groups based on the calculated distances.

4. The method according to claim 3, wherein constructing the feature vector further includes at least one of:
    splitting, by one or more processors, a first attribute of the plurality of attributes into a plurality of second attributes, wherein each of the plurality of second attributes is used to construct an element of the feature vector.

5. The method according to claim 4, wherein the first attribute is a clinical attribute.

6. The method according to claim 1, wherein the set of data instances are patient instances.

7. The method according to claim 2, wherein the plurality of attributes include at least one demographic attribute and at least one clinical attribute.

8. A system for two-stage data instance processing, the system comprising:
    one or more processors;
    a memory coupled to at least one of the one or more processors;
    a network interface coupling the one or more processors to processors of a plurality of organizations over a network;
    a set of computer program instructions stored in the memory and executed by at least one of the one or more processors in order to perform actions of:
    obtaining a set of data instances collected over the network from the plurality of organizations, wherein each of the data instances includes at least one record formed in an organization of the plurality of organizations that stores values of a plurality of attributes of the data instance;

preliminarily dividing, in stage one, conflict detection using the one or more processors, the set of data instances into groups within the memory, wherein data instances with conflicting values for the same attribute are divided into different groups and stored on a remote server in a distributed cloud computing environment;

subdividing, in stage two, data instances in each of the groups into clusters to increase precision of the dividing, the subdividing comprising constructing, by one or more processors, for each of the data instances in each of the groups, a feature vector based on the at least one record of the data instance for further processing, with the values of the plurality of attributes being transformed into binary values for increased efficiency of the processing and minimization of bandwidth and memory requirements; and creating a new electronic record having the transformed binary values of the plurality of attributes of the data instances in the cluster by combining the data instances in each cluster, the electronic record being updated on a local machine and stored on the remote server in the distributed cloud computing environment to minimize network bandwidth and local machine memory requirements for efficient iterative accessing and maintaining of the record.

9. The system according to claim 8, wherein dividing the set of data instances into groups further includes:

for each data instance in the set of data instances, forming a value sequence based on the at least one record of the data instance, wherein the value sequence includes selected attributes as its elements;

constructing a conflict network in which a data instance is represented by a node and there is an edge between two nodes if two data instances represented by the two nodes have at least one conflicting element in their value sequences; and assigning labels to nodes of the conflict network with minimum labels, wherein nodes directly connected by an edge in the conflict network have different labels, and data instances represented by nodes with a same label are divided into a same group.

10. The system according to claim 8, wherein subdividing data instances in each of the groups into clusters further includes:

calculating distances between every two feature vectors; and clustering the data instances in each of the groups based on the calculated distances.

11. The system according to claim 10, wherein constructing the feature vector further includes at least one of:

splitting a first attribute of the plurality of attributes into a plurality of second attributes, wherein each of the plurality of second attributes is used to construct at ent of the feature vector.

12. The system according to claim 11, wherein the first attribute is a clinical attribute.

13. The system according to claim 8, wherein the set of data instances are patient instances.

14. The system according to claim 9, wherein the plurality of attributes include at least one demographic attribute and at least one clinical attribute.

15. A computer program product for data instance processing, the computer program product comprising a computer readable storage medium having program instructions embodied therewith, wherein the program instructions being executable by one or more processor devices to cause the device to perform a method comprising:

obtaining a set of data instances collected from a plurality of organizations over a network, wherein each of the data instances includes at least one record formed in an organization of the plurality of organizations that stores values of a plurality of attributes of the data instance;

preliminarily dividing, in stage one, by conflict detection using at least one of the one or more processors, the set of data instances into groups, wherein data instances with conflicting values for the same attribute are divided into different groups and stored on a remote server in a distributed cloud computing environment;

subdividing, in stage two, data instances in each of the groups into clusters to increase precision of the dividing, the subdividing comprising constructing, by one or more processors, for each of the data instances in each of the groups, a feature vector based on the at least one record of the data instance for further processing, with the values of the plurality of attributes being transformed into binary values for increased efficiency of the processing and minimization of bandwidth and memory requirements; and creating a new electronic record comprising the transformed binary values of the plurality of attributes of the data instances in the cluster by combining the data instances in each cluster, the electronic record being updated on a local machine and stored on the remote server in the distributed cloud computing environment to minimize network bandwidth and local machine memory requirements for efficient iterative accessing and maintaining of the record.

16. The computer program product according to claim 15, wherein dividing the set of data instances into groups further includes:

for each data instance in the set of data instances, forming a value sequence based on the at least one record of the data instance, wherein the value sequence includes selected attributes as its elements;

constructing a conflict network in which a data instance is represented by a node and there is an edge between two nodes if two data instances represented by the two nodes have at least one conflicting element in their value sequences; and assigning labels to nodes of the conflict network with minimum labels, wherein nodes directly connected by an edge in the conflict network have different labels, and data instances represented by nodes with a same label are divided into a same group.

17. The computer program product according to claim 15, wherein subdividing data instances in each of the groups into clusters further includes:

calculating distances between every two feature vectors; and clustering the data instances in each of the groups based on the calculated distances.

18. The computer program product according to claim 17, wherein constructing the feature vector further includes at least one of:

splitting a first attribute of the plurality of attributes into a plurality of second attributes, wherein each of the plurality of second attributes is used to construct an element of the feature vector.

19. The computer program product according to claim 15, the set of data instances are patient instances.

20. The computer program product according to claim 16, wherein the plurality of attributes include at least one demographic attribute and at least one clinical attribute.

\* \* \* \* \*